(12) United States Patent
Dabrowska et al.

(10) Patent No.: US 10,160,956 B2
(45) Date of Patent: Dec. 25, 2018

(54) METHOD OF PRODUCING BACTERIOPHAGE PREPARATIONS COMPRISING PURIFICATION USING AFFINITY CHROMATOGRAPHY

(76) Inventors: Krystyna Dabrowska, Wroclaw (PL); Anna Oslizlo, Nysa (PL); Paulina Budynek, Glucholazy (PL); Agnieszka Otrowicz, Wroclaw (PL); Andrzej Gorski, Wroclaw (PL); Grzegorz Figura, Brzeg (PL); Barbara Owczarek, Wroclaw (PL); Agnieszka Kopciuch, Ligota Piekna (PL)

( * ) Notice: Subject to any disclaimer, the term of this patent is extended or adjusted under 35 U.S.C. 154(b) by 0 days.

(21) Appl. No.: 13/881,795

(22) PCT Filed: Oct. 28, 2011

(86) PCT No.: PCT/PL2011/050044
§ 371 (c)(1),
(2), (4) Date: Jul. 15, 2013

(87) PCT Pub. No.: WO2012/057643
PCT Pub. Date: May 3, 2012

(65) Prior Publication Data
US 2013/0295647 A1 Nov. 7, 2013

(30) Foreign Application Priority Data
Oct. 28, 2010 (PL) .......................................... 392774

(51) Int. Cl.
*C12N 7/00* (2006.01)
*C07K 14/005* (2006.01)

(52) U.S. Cl.
CPC .............. *C12N 7/00* (2013.01); *C07K 14/005* (2013.01); *C07K 2319/21* (2013.01); *C07K 2319/23* (2013.01); *C12N 2795/00051* (2013.01); *C12N 2795/10122* (2013.01); *C12N 2795/10151* (2013.01)

(58) Field of Classification Search
CPC ............ C07K 2317/73; C07K 2319/00; C07K 2319/21; C07K 2319/23; C12N 15/1034; C12N 7/00; C40B 40/08; C40B 40/10; C40B 50/06; G01N 33/569; G01N 33/6845
See application file for complete search history.

(56) References Cited

U.S. PATENT DOCUMENTS

2007/0178576 A1* 8/2007 Demmer ................... C07K 1/22
435/239
2007/0224622 A1* 9/2007 Jones ................... C07K 14/415
435/6.14

FOREIGN PATENT DOCUMENTS

| WO | WO 2007/064462 | * | 7/2007 |
| WO | WO2010/030425 | * | 3/2010 |
| WO | 2011162627 A1 | | 12/2011 |

OTHER PUBLICATIONS

Mecconti's Dehydrated Culture Media Product Listing (Apr. 2, 2008).*
GenBank Accession No. X01774.1 (Apr. 20, 1993).*
Udit et al., "Immobilization of bacteriophage Qβ on metal-derivatized surfces via polyvalent display of hexahistidine tags," Journal of Inorganic Biochemistry (2008) 102:2142-2146.
Oslizlo et al., "Purification of phage display-modified bacteriophage T4 by affinity chromatography," BMC Technology (2011) 11:59, pp. 1472-6750.
Jiang et al., "Display of a porA peptide from neisseria meningitidis on the bacteriophage T4 capsid surface," Infection and Immunity (1997) 65(11):4770-4777.

* cited by examiner

*Primary Examiner* — Nicole Kinsey White
(74) *Attorney, Agent, or Firm* — Fox Rothschild LLP

(57) ABSTRACT

The proposed method facilitates the single-stage and at the same time effective purification of phage preparations for therapeutic uses, and facilitates the maintenance of bacteriophage antibacterial activity both in the case of displacement of the bacteriophage from the resin and its proteolytic release. The protein modification of the phage capsid with appropriate binding motifs makes it possible to purify therapeutically bacteriophage strains using affinity chromatography. The proposed method is useful in the display of selected polypeptided on a bacteriophage capsid without the need to genetically modify the bacteriophage, and thus makes it possible to produce phage preparations for various uses using wild-type phages occurring naturally or others not additionally modified for phage-display purposes.

7 Claims, 6 Drawing Sheets
Specification includes a Sequence Listing.

HOC gene sequence:

```
ATGACTTTTACAGTTGATATAACTCCTAAAACACCTACAGGGGTTATTGATGAAACTAAGCAGTTTACTGCTACA
CCCAGTGGTCAAACTGGAGGCGGAACTATTACATATGCTTGGAGCGTAGATAATGTTCCACAAGATGGAGCTGAA
GCAACTTTTAGTTATGTACTAAAAGGACCTGCCGGTCAAAAGACTATTAAAGTAGTTGCAACAAATACACTTTCT
GAAGGAGGCCCGGAAACGGCTGAAGCGACAACAACTATCACAGTTAAAAATAAGACACAGACGACTACCTTAGCC
GTAACTCCTGCTAGTCCTGCGGCTGGAGTGATTGGAACCCCAGTTCAATTTACTGCTGCCTTAGCTTCTCAACCT
GATGGAGCATCTGCTACGTATCAGTGGTATGTAGATGATTCACAAGTTGGTGGAGAAACTAACTCTACATTTAGC
TATACTCCAACTACAAGTGGAGTAAAAAGAATTAAATGCGTAGCCCAAGTAACCGCGACAGATTATGATGCACTA
AGCGTTACTTCTAATGAAGTATCATTAACGGTTAATAAGAAGACAATGAATCCACAGGTTACATTGACTCCTCCT
TCTATTAATGTTCAGCAAGATGCTTCGGCTACATTTACGGCTAATGTTACGGGTGCTCCAGAAGAAGCACAAATT
ACTTACTCATGGAAGAAAGATTCTTCTCCTGTAGAAGGGTCAACTAACGTATATACTGTCGATACCTCATCTGTT
GGAAGTCAAACTATTGAAGTTACTGCAACTGTTACTGCTGCAGATTATAACCCTGTAACCGTTACCAAAACTGGT
AATGTAACAGTCACGGCTAAAGTTGCTCCAGAACCAGAAGGTGAATTACCTTATGTTCATCCTCTTCCACACCGT
AGCTCAGCTTACATCTGGTGCGGTTGGTGGGTTATGGATGAAATCCAAAAAATGACCGAAGAAGGTAAAGATTGG
AAAACTGACGACCCAGATAGTAAATATTACCTGCATCGTTACACTCTCCAGAAGATGATGAAAGACTATCCAGAA
GTTGATGTCCAAGAATCGCGTAATGGATACATCATTCATAAAACTGCTTTAGAAACTGGTATCATCTATACCTAT
CCATAA (SEQ ID NO: 1)
```

Fig. 1

Expression casette – Hoc protein fused with GST – expected HocGST product mass: 66 kDa

| T7 Promotor | RBS (Riboso Binding Side) | GST | digestion site for AcTEV | 3xSer | HOC | T7 Terminato |
|---|---|---|---|---|---|---|

Bold print highlights sequences from the vector pDEST15 (Invitrogen), underlining the restriction sites characteristic of the vector pDEST15
Normal print describes the remaining operatorelements, additionally shown with the following markings: single underline: T7 promoter, double underline: RBS, dashed underline: GST, zigzag underline: T7 terminator;
*Italics denote a construct that contains the HOC gene, encompassing cleavage sites for AcTev (single underline), 3xSer (double underline), HOC gene (dashed underline)*

TAATACGACTCACTATAGGGAGACCACAACGGTTTCCCTCTAGAAATAATTTTGTTTAACTTTAAGAAGGAGATA TACATATGTCCCCTATACTAGGTTATTGGAAAATTAAGGGCCTTGTGCAACCCACTCGACTTCTTTTGGAATATC TTGAAGAAAAATATGAAGAGCATTTGTATGAGCGCGATGAAGGTGATAAATGGCGAAACAAAAAGTTTGAATTGG GTTTGGAGTTTCCCAATCTTCCTTATTATATTGATGGTGATGTTAAATTAACACAGTCTATGGCCATCATACGTT ATATAGCTGACAAGCACAACATGTTGGGTGGTTGTCCAAAAGAGCGTGCAGAGATTTCAATGCTTGAAGGAGCGG TTTTGGATATTAGATACGGTGTTTCGAGAATTGCATATAGTAAAGACTTTGAAACTCTCAAAGTTGATTTTCTTA GCAAGCTACCTGAAATGCTGAAAATGTTCGAAGATCGTTTATGTCATAAAACATATTTAAATGGTGATCATGTAA CCCATCCTGACTTCATGTTGTATGACGCTCTTGATGTTGTTTATACATGGACCCAATGTGCCTGGATGCGTTCC CAAAATTAGTTTGTTTTAAAAAACGTATTGAAGCTATCCCACAAATTGATAAGTACTTGAAATCCAGCAAGTATA TAGCATGGCCTTTGCAGGGCTGGCAAGCCACGTTTGGTGGTGGCGACCATCCTCCAAAATCGGATCTGGTTCCGC GTCCATGGTCGAATCAAACAAGTTTGTACAAAAAAGCAGGCT

*GAAAACCTGTATTTTCAGGGCTCATCATCAA*TGACTTTTACAGTTGATATAACTCCTAAAACACCTACAGGGGTT ATTGATGAAACTAAGCAGTTTACTGCTACACCCAGTGGTCAAACTGGAGGCGGAACTATTACATATGCTTGGAGC GTAGATAATGTTCCACAAGATGGAGCTGAAGCAACTTTTAGTTATGTACTAAAAGGACCTGCCGGTCAAAAGACT ATTAAAGTAGTTGCAACAAATACACTTTCTGAAGGAGGCCCGGAAACGGCTGAAGCGACAACAACTATCACAGTT AAAAATAAGACACAGACGACTACCTTAGCCGTAACTCCTGCTAGTCCTGCGGCTGGAGTGATTGGAACCCCAGTT CAATTTACTGCTGCCTTAGCTTCTCAACCTGATGGAGCATCTGCTACGTATCAGTGGTATGTAGATGATTCACAA GTTGGTGGAGAAACTAACTCTACATTTAGCTATACTCCAACTACAAGTGGAGTAAAAGAATTAAATGCGTAGCC CAAGTAACCGCGACAGATTATGATGCACTAAGCGTTACTTCTAATGAAGTATCATTAACGGTTAATAAGAAGACA ATGAATCCACAGGTTACATTGACTCCTCCTTCTATTAATGTTCAGCAAGATGCTTCGGCTACATTTACGGCTAAT GTTACGGGTGCTCCAGAAGAAGCACAAATTACTTACTCATGGAAGAAAGATTCTTCTCCTGTAGAAGGGTCAACT AACGTATATACTGTCGATACCTCATCTGTTGGAAGTCAAACTATTGAAGTTACTGCAACTGTTACTGCTGCAGAT TATAACCCTGTAACCGTTACCAAAACTGGTAATGTAACAGTCACGGCTAAAGTTGCTCCAGAACCAGAAGGTGAA TTACCTTATGTTCATCCTCTTCCACACCGTAGCTCAGCTTACATCTGGTGCGGTTGGTGGGTTATGGATGAAATC CAAAAAATGACCGAAGAAGGTAAAGATTGGAAAACTGACGACCCAGATAGTAAATATTACCTGCATCGTTACACT CTCCAGAAGATGATGAAAGACTATCCAGAAGTTGATGTCCAAGAATCGCGTAATGGATACATCATTCATAAAACT GCTTTAGAAACTGGTATCATCTATACCTATCCATAA*

ACCCAGCTTTCTTGTACAAAGTGGTTTGATTCGACCCGGGATCCGGCTGCTAACAAAGCCCGAAAGGAATAGCAT AACCCCTTGGGGCCTCTAAACGGGTCTTGAGGGGTTTTTTG (SEQ ID NO: 2)

Fig. 2

Expression casette – Hoc protein fused with Histag – expected HocHistag

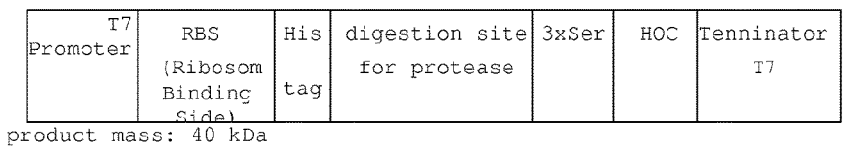

product mass: 40 kDa

Bold print highlights sequences from the vector pDEST15 (Invitrogen), underlining the
restriction sites characteristic of the vector pDEST15
Normal print describes the remaining operatorelements, additionally shown with the following
markings: single underline: T7 promoter, double underline: RBS, dashed underline: GST, zigzag
underline: T7 terminator;
*Italics denote a construct that contains the HOC gene, encompassing cleavage sites for AcTev
(single underline), 3xSer (double underline), HOC gene (dashed underline)*

TAATACGACTCACTATAGGGAGACCACAACGGTTTCCCTCTAGAAATAATTTTGTTTAACTTTAAGAAGGAGATA
TACATATGTCGTACTACCATCACCATCACCATCACCTCGAATCAACAAGTTTGTACAAAAAAGCAGGCT
*GAAAACCTGTATTTTCAGGGCTCATCATCAATGACTTTTACAGTTGATATAACTCCTAAAACACCTACAGGGGTT*
*ATTGATGAAACTAAGCAGTTTACTGCTACACCCAGTGGTCAAACTGGAGGCGGAACTATTACATATGCTTGGAGC*
*GTAGATAATGTTCCACAAGATGGAGCTGAAGCAACTTTTAGTTATGTACTAAAAGGACCTGCCGGTCAAAAGACT*
*ATTAAAGTAGTTGCAACAAATACACTTTCTGAAGGAGGCCCGGAAACGGCTGAAGCGACAACAACTATCACAGTT*
*AAAAATAAGACACAGACGACTACCTTAGCCGTAACTCCTGCTAGTCCTGCGGCTGGAGTGATTGGAACCCCAGTT*
*CAATTTACTGCTGCCTTAGCTTCTCAACCTGATGGAGCATCTGCTACGTATCAGTGGTATGTAGATGATTCACAA*
*GTTGGTGGAGAAACTAACTCTACATTTAGCTATACTCCAACTACAAGTGGAGTAAAAAGAATTAAATGCGTAGCC*
*CAAGTAACCGCGACAGATTATGATGCACTAAGCGTTACTTCTAATGAAGTATCATTAACGGTTAATAAGAAGACA*
*ATGAATCCACAGGTTACATTGACTCCTCCTTCTATTAATGTTCAGCAAGATGCTTCGGCTACATTTACGGCTAAT*
*GTTACGGGTGCTCCAGAAGAAGCACAAATTACTTACTCATGGAAGAAAGATTCTTCTCCTGTAGAAGGGTCAACT*
*AACGTATATACTGTCGATACCTCATCTGTTGGAAGTCAAACTATTGAAGTTACTGCAACTGTTACTGCTGCAGAT*
*TATAACCCTGTAACCGTTACCAAAACTGGTAATGTAACAGTCACGGCTAAAGTTGCTCCAGAACCAGAAGGTGAA*
*TTACCTTATGTTCATCCTCTTCCACACCGTAGCTCAGCTTACATCTGGTGCGGTTGGTGGGTTATGGATGAAATC*
*CAAAAATGACCGAAGAAGGTAAAGATTGGAAAACTGACGACCCAGATAGTAAATATTACCTGCATCGTTACACT*
*CTCCAGAAGATGATGAAAGACTATCCAGAAGTTGATGTCCAAGAATCGCGTAATGGATACATCATTCATAAAACT*
*GCTTTAGAAACTGGTATCATCTATACCTATCCATAA*
ACCCAGCTTTCTTGTACAAAGTGGTTGATTCGAGGCTGCTAACAAAGCCCGAAAGGAAGTAGCATAACCCCTTGG
GGCCTCTAAACGGGTCTTGAGGGGTTTTTTG (SEQ ID NO: 3)

Fig. 3

Panel A

Panel B

Panel C

Panel D

SEQUENCE LISTING

<160> NUMBER OF SEQ ID NOS: 3

<210> SEQ ID NO 1
<211> LENGTH: 1371
<212> TYPE: DNA
<213> ORGANISM: Bacteriophage T4

<400> SEQUENCE: 1

```
gctgaaatcg gtggtgacca cggttacaat gctaccaaca tcgctgcagg tcagacttct      60
ggcgcagtaa ctcagattgg cccagctgtt atgggtatgt tacgtcgtgc tattcctaac     120
ctgattgctt tcgatatttg tggtgttcag ccgatgaaca gcccgactgg ccaggtattc     180
gcactgcgcg cagtatatgg taaagaccca gtggctgccg gtgctaaaga agcattccac     240
ccaatgtatg gtccagatgc aatgttctct ggtcagggtg ctgctaagaa attcccagct     300
ctggctgcta gcacacaaac cacagtaggt gatatctata ctcacttctt ccaggaaact     360
ggtactgtat atctgcaagc ttctgttcaa gtaacaatcg atgctggtgc gactgatgct     420
gctaaattag atgctgaaat taagaaacaa atggaagctg gtgcactggt agaaatcgct     480
gaaggtatgg ctacttctat cgctgaactc caggaaggtt tcaatggttc taccgataac     540
ccatggaatg aaatgggctt ccgtatcgat aagcaagtta tcgaagctaa atctcgtcag     600
ctgaaagctg cttactctat tgaattagca caagacctcc gcgctgttca cggtatggat     660
gctgatgctg aactgtctgg tattctggct acagaaatta tgctggaaat caaccgtgaa     720
gttgttgatt ggattaacta ctcagctcag gttggtaaat ctggtatgac cctgactccg     780
ggttctaaag ctggtgtatt tgacttccag gacccaattg atattcgtgg tgctcgctgg     840
gcgggtgaat cctttaaagc tctgttgttc cagattgaca agaagcagt tgaaattgct     900 cgtcagaccg gtcgtggtga aggtaacttc attatcgctt cccgtaacgt agttaacgtt     960
ttggcttcag ttgataccgg catttcttat gctgcacagg gtctggctac cggctttagc    1020
actgatacta ccaagtcagt atttgctggt gttctgggtg gtaaataccg cgtatatatc    1080
gaccagtatg ctaaacagga ttatttcact gtaggttata aaggtccgaa cgaaatggat    1140
gctggtattt actatgctcc atatgtagct ctgactccgc tgcgtggttc cgatccgaag    1200
aacttccaac cggtaatggg attcaaaact cgttacggta tcggtatcaa cccatttgca    1260
gaatccgctg ctcaggctcc ggcttctcgc atccagagcg gtatgccttc tattctgaat    1320
agccttggta aaaacgctta ctttagacgt gtatatgtta aaggtatcta a             1371
```

<210> SEQ ID NO 2
<211> LENGTH: 2309
<212> TYPE: DNA
<213> ORGANISM: Artificial
<220> FEATURE:
<223> OTHER INFORMATION: Synthetic expression cassette: protein gp23*
      fused with GST

<400> SEQUENCE: 2

```
taatacgact cactataggg agaccacaac ggtttccctc tagaaataat tttgtttaac      60
tttaagaagg agatatacat atgtccccta tactaggtta ttggaaaatt aagggccttg     120
tgcaacccac tcgacttctt ttggaatatc ttgaagaaaa atatgaagag catttgtatg     180
agcgcgatga aggtgataaa tggcgaaaca aaaagtttga attgggtttg gagttttcca     240
atcttcctta ttatattgat ggtgatgtta aattaacaca gtctatggcc atcatacgtt     300
atatagctga caagcacaac atgttgggtg gttgtccaaa agagcgtgca gagatttcaa     360
tgcttgaagg agcggttttg gatattagat acggtgtttc gagaattgca tatagtaaag     420
actttgaaac tctcaaagtt gattttctta gcaagctacc tgaaatgctg aaaatgttcg     480
aagatcgttt atgtcataaa acatatttaa atggtgatca tgtaacccat cctgacttca     540
tgttgtatga cgctcttgat gttgttttat acatggaccc aatgtgcctg gatgcgttcc     600
caaaattagt ttgttttaaa aaacgtattg aagctatccc acaaattgat aagtacttga     660
aatccagcaa gtatatagca tggcctttgc agggctggca agccacgttt ggtggtggcg     720
accatcctcc aaaatcggat ctggttccgc gtccatggtc gaatcaaaca gtttgtaca     780
aaaaagcagg ctgaaaacct gtattttcag ggctcatcat cagctgaaat cggtggtgac     840
cacggttaca atgctaccaa catcgctgca gtcagactt ctggcgcagt aactcagatt     900
ggcccagctg ttatgggtat ggtacgtcgt gctattccta acctgattgc tttcgatatt     960
tgtggtgttc agccgatgaa cagcccgact ggccaggtat cgcactgcg cgcagtatat    1020
ggtaaagacc cagtggctgc cggtgctaaa gaagcattcc acccaatgta tggtccagat    1080
gcaatgttct ctggtcaggg tgctgctaag aaattcccag ctctggctgc tagcacacaa    1140
accacagtag gtgatatcta tactcacttc ttccaggaaa ctggtactgt atatctgcaa    1200
gcttctgttc aagtaacaat cgatgctggt gcgactgatg ctgctaaatt agatgctgaa    1260
attaagaaac aaatggaagc tggtgcactg gtagaaatcg ctgaaggtat ggctacttct    1320
atcgctgaac tccaggaagg tttcaatggt tctaccgata acccatggaa tgaaatgggc    1380
ttccgtatcg ataagcaagt tatcgaagct aaatctcgtc agctgaaagc tgcttactct    1440
attgaattag cacaagacct ccgcgctgtt cacggtatgg atgctgatgc tgaactgtct    1500
ggtattctgg ctacagaaat tatgctggaa atcaaccgtg aagttgttga ttggattaac    1560
tactcagctc aggttggtaa atctggtatg accctgactc cgggttctaa agctggtgta    1620
tttgacttcc aggacccaat tgatattcgt ggtgctcgct gggcgggtga atcctttaaa    1680
gctctgttgt tccagattga caaagaagca gttgaaattg ctcgtcagac cggtcgtggt    1740
gaaggtaact tcattatcgc ttcccgtaac gtagttaacg tttttggcttc agttgatacc    1800
ggcatttctt atgctgcaca gggtctggct accggcttta gcactgatac taccaagtca    1860
gtatttgctg gtgttctggg tggtaaatac cgcgtatata tcgaccagta tgctaaacag    1920
gattatttca ctgtaggtta taaggtccg aacgaaatgg atgctggtat ttactatgct    1980
ccatatgtag ctctgactcc gctgcgtggt tccgatccga agaacttcca accggtaatg    2040
```

```
ggattcaaaa ctcgttacgg tatcggtatc aacccatttg cagaatccgc tgctcaggct    2100
ccggcttctc gcatccagag cggtatgcct tctattctga atagccttgg taaaaacgct    2160
tactttagac gtgtatatgt taaaggtatc taaacccagc tttcttgtac aaagtggttt    2220
gattcgaccc gggatccggc tgctaacaaa gcccgaaagg aatagcataa ccccttgggg    2280
cctctaaacg ggtcttgagg ggttttttg                                      2309
```

<210> SEQ ID NO 3
<211> LENGTH: 1651
<212> TYPE: DNA
<213> ORGANISM: Artificial
<220> FEATURE:
<223> OTHER INFORMATION: Synthetic expression cassette: protein 23* fused with Histag

<400> SEQUENCE: 3

```
taatacgact cactataggg agaccacaac ggtttccctc tagaaataat tttgtttaac      60
tttaagaagg agatatacat atgtcgtact accatcacca tcaccatcac ctcgaatcaa     120
caagtttgta caaaaaagca ggctgaaaac ctgtattttc agggctcatc atcagctgaa     180
atcggtggtg accacggtta caatgctacc aacatcgctg caggtcagac ttctggcgca     240
gtaactcaga ttggcccagc tgttatgggt atggtacgtc gtgctattcc taacctgatt     300
gctttcgata tttgtggtgt tcagccgatg aacagcccga ctggccaggt attcgcactg     360
cgcgcagtat atggtaaaga cccagtggct gccggtgcta agaagcatt ccacccaatg      420 tatggtccag atgcaatgtt ctctggtcag ggtgctgcta gaaattccc agctctggct      480 gctagcacac aaaccacagt aggtgatatc tatactcact tcttccagga aactggtact     540
gtatatctgc aagcttctgt tcaagtaaca atcgatgctg gtgcgactga tgctgctaaa     600
ttagatgctg aaattaagaa acaaatggaa gctggtgcac tggtagaaat cgctgaaggt     660
atggctactt ctatcgctga actccaggaa ggtttcaatg ttctaccga taacccatgg      720 aatgaaatgg gcttccgtat cgataagcaa gttatcgaag ctaaatctcg tcagctgaaa     780
gctgcttact ctattgaatt agcacaagac ctccgcgctg ttcacggtat ggatgctgat     840
gctgaactgt ctggtattct ggctacagaa attatgctgg aaatcaaccg tgaagttgtt     900
gattggatta actactcagc tcaggttggt aaatctggta tgaccctgac tccgggttct     960
aaagctggtg tatttgactt ccaggaccca attgatattc gtggtgctcg ctgggcgggt    1020
gaatccttta agctctgtt gttccagatt gacaaagaag cagttgaaat tgctcgtcag     1080
accggtcgtg gtgaaggtaa cttcattatc gcttcccgta acgtagttaa cgttttggct    1140
tcagttgata ccggcatttc ttatgctgca cagggtctgg ctaccggctt tagcactgat    1200
actaccaagt cagtatttgc tggtgttctg ggtggtaaat accgcgtata tatcgaccag    1260
tatgctaaac aggattattt cactgtaggt tataaaggtc gaacgaaat ggatgctggt      1320 atttactatg ctccatatgt agctctgact ccgctgcgtg gttccgatcc gaagaacttc    1380
caaccggtaa tgggattcaa aactcgttac ggtatcggta tcaacccatt tgcagaatcc    1440
gctgctcagg ctccggcttc tcgcatccag agcggtatgc cttctattct gaatagcctt    1500
ggtaaaaacg cttactttag acgtgtatat gttaaaggta tctaaaccca gctttcttgt    1560
acaaagtggt tgattcgagg ctgctaacaa agcccgaaag gaagtagcat aaccccttgg    1620
ggcctctaaa cgggtcttga ggggttttt g                                    1651
```

METHOD OF PRODUCING BACTERIOPHAGE PREPARATIONS COMPRISING PURIFICATION USING AFFINITY CHROMATOGRAPHY

This application is a U.S. National Phase Application of International Application No. PCT/PL2011/050044 filed Oct. 28, 2011, which claims priority to Polish Application No. 392774 filed Oct. 28, 2010, the disclosures of which are hereby incorporated by reference in their entirety.

The present invention relates to a method of producing bacteriophages exhibiting foreign proteins or peptides on their surface without the need to interfere in the phage genome and without the need to use phage strains deficient in particular genes (the method does not require genetically modified strains). The resulting bacteriophage preparations have many uses particularly in the purification of bacteriophages for the manufacture of products requiring high purity such as medicinal products, and in the manufacture of bacteriophages expressing particular peptides or proteins for other purposes, i.e. in vaccine manufacturing.

During the lytic cycle, during therapy, bacteria are destroyed by the bacteriophages replicating within them. Bacteriophage progeny, in greatly multiplied numbers, are then released into the environment, which then lyse subsequent bacterial populations.

In the case of bacteriophage lysates for biotechnological purposes, not only the numbers of bacteriophage progeny are important, but also the bacterial constituents released, such as nucleic acids, proteins and cell wall components. The wall of Gram-negative bacteria is composed of a significant percentage (as much as 70%) of lipopolysaccharides (called pyrogens, endotoxins), peptides and proteins.

The effective removal of pyrogens and active proteins from bacterial lysates is a key requirement of producing bacteriophage preparations dedicated for bacterial infection therapy. Endotoxins arestrong stimulators of the immune system and induce the production of interleukins, TNF, NO, etc.

Endotoxin removal and isolation procedures are based on extraction using organic solvents such as aqueous phenol Westphal O., Lueritz O., Bister F. Uber die Extraktion von Bakterien mit Phenol/wasser. Z. Naturforsch. 7: 148-155, 1952), aliphatic amine and acid mixtures (Patent application Publicatiom U.S. 2007/0020292A1), extractive and chromatographic methods (Patent Application publication U.S. 2007/0031447 Al). The elimination of endotoxins from biological preparations has been performed using metal ion interactions with proteins (patent U.S. Pat. No. 6,942,802 B2 Sep. 13, 2005; W002083710A1; W004003215A1), through the precipitation of endotoxins with alcohol and bivalent counterions (U.S. Pat. No. 5,039,610). The use of bivalent ions in combination with alcohols, resins and detergents is the subject of many patents, such as for example EPO 407037B1. Endotoxin removal has been performed using crab lymph proteins (U.S. Pat. No. 5,760,177). Many column chromatography methods have been described. They make use of the affinity of lipopolysaccharides for the haptens used such as polymyxine (Petsch D, Beeskow T C, Anspach F B, Deckwer W D, (1997) Membrane adsorbers for selective removal of bacterial endotoxin. J. Chromatogr B Biomed Sci Appl. 693(1):79-91), a calcium silicate resin (Hang J P, Wang Q, Smith T R, Hurst W E, Sulpizio T, (2005) Endotoxin removal using a synthetic adsorbent of crystalline calcium silicate hydrate. Biotechnol Prago 21(4): 1220-5), synthetic polymers (Hirayama Ch, Sakata M, (2002) Chromatographic removal of endotoxin from protein solutions by polymer particles. Journal oj Chramatography B, 781:419-432) or polyanionic beds (Boratyński J, Syper D, Weber-Dabrowska B, Ł usiak-Szelachowska M, Poźniak G, Górski A. Preparation of endotoxin-free bacteriophages Cell Mol Biol Lett. 2004; 9(2):253-9).

There is still a great need for the delivery of a method of purifying bacteriophage lysates, particularly of endotoxins, which could be used for the industrial production of bacteriophage preparations meant for use in the treatment of bacterial infections in humans. The initial titres of unpurified lysates may contain LPS with an activity of $10^4$-$10^5$. Despite the multiple methods of purifying bacteriophage lysates described above, significantly fail to meet the requirements of the industrial production of preparations for the above.

The phage display method of expressing a given protein or peptide on a bacteriophage capsid is based on (i) the introduction of genes encoding these proteins or peptides into the bacteriophage genome (creation of a GMO) or (i) the use of a bacteriophage strain deficient in terms of a selected gene encoding a protein not essential to the bacteriophage and the subsequent supplementation of this lack using recombinant proteins expressed from vector constructs, usually in a bacterial system (creation of a strain with a deletion of the selected gene). In both cases the display of the protein or peptide requires the previous genetic modification of the host strain.

Unexpectedly, a method fulfilling the above requirements made of industrial methods of producing purified phage preparations, and at the same time facilitating the display of foreign peptides or proteins on the phage capsid without introducing changes into the phage genome (also on wild-type phage) is proposed in the present invention.

The subject of the present invention is a method of producing bacteriophages characterised in that:
a) a bacterial host is cultured in an appropriate medium, the culture is inoculated with a bacteriophage and a bacteriophage lysate is obtained for further purification or other uses
b) the bacteriophage lysate is purified using affinity chromatography, d) and the purified bacteriophage preparation is obtained from the resulting eluate,
wherein in stage a) the bacterial host strain used consists of bacterial cells containing a sequence encoding fusion proteins being components of the bacteriophage capsid present in the resulting lysate with (i) a polypeptide exhibiting affinity for the chromatography resin used in stage b), if the goal is the production of a purified bacteriophage preparation or (i) another polypeptide with the required activity, if the goal is the presentation of other active motifs.

Preferably, the bacteriophage strain modified and/or purified according to this method may be any given wild-type strain, not genetically modified. Particularly preferably, the culture is inoculated with a bacteriophage strain not genetically modified for the phage-display method, meaning a wild-type bacteriophage or one modified for another purpose, wherein said bacteriophage displays foreign polypeptides on its surface.

Preferably, the polypeptide which facilitates the purification of bacteriophages, which exhibits affinity for the chromatography resin is selected from a group encompassing HisTag and GST. PAn example polypeptide derived from a phage structural protein is encoded by a sequence encoding protein gp23*, the mature form of the main capsid protein gp23* (following proteolytic cleavage during the maturation of the head). This sequence is shown is in FIG. 1.

Preferably, during stage a) the bacterial host strain used is a bacterial strain sensitive to the lytic activity of the amplified bacteriophage.

Preferably, during stage a) the resulting phage lysate is filter-sterilised by a 0.22 μm sterilizing filter.

Affinity chromatography is a well established, very efficient purification strategy for proteins from various sources. Unexpectedly, the use of this method in the method according to the present invention of isolating whole bacteriophage capsids (complex and extensive protein complexes) made it possible to retain the antibacterial activity of the isolated bacteriophages, despite the fact that the capsids were extensively modified to enable them to be used in affinity chromatography. In the example embodiment we used the phage display technique to introduce binding motifs into the phage capsid and then we based on the binding of such modified bacteriophages to the affinity resin selected appropriately for a selected bnding motif.

The description has been supplemented with the following figures:

FIG. 1 shows the sequence of a fragment of the 23 gene encoding the mature form of the main capsid protein gp23* (post-proteolytic cleavage);

FIG. 2 shows an expression cassette: protein gp23* fused with GST—wherein the expected mass of the 23*GST product is 78 kDa; the sequences from the vector pDEST15 (Invitrogen) are shown in bold, with characteristic recombination sites for the vector pDEST15 shown underlined, normal typeface defines remaining operator elements, with the following additional markings: single underline: n promoter, double underline: RBS, dashed underline: GST, zigzag underline: n terminator; italics denote the construct containing the gene 23* necompassing AcTev cleavage sites (single underline), 3×Ser (double underline), gen 23* (dashed underline).

FIG. 3 shows the expression cassette—protein 23* fused with Histag—wherein the expected mass of the 23*Histag product is 50 kDa; the sequences from the vector pDEST15 (Invitrogen) are shown in bold, with characteristic recombination sites for the vector pDEST15 shown underlined, normal typeface defines remaining operator elements, with the following additional markings: single underline: n promoter, double underline: RBS, dashed underline: Histag, zigzag underline: n terminator; italics denote the construct containing the gene 23* necompassing AcTev cleavage sites (single underline), 3×Ser (double underline), gen 23* (dashed underline);

FIG. 4 shows the expression of the protein gp23* and gpWac fused with GST and Histag in *E. coli* Rosetta cells (panels A, B, C, D), Panel A—image of gel post Electrophoresis—protein profile after the lysis of cells expressing the protein 23* fused with Histag:1—mass marker (Fermentas SM0661), 2,3,4-unrelated, 5-23*Histag 3 h post-induction with IPTG (the product is pointed out with an arrow), Panel B—electrophoretic gel image—protein profile following the lysis of cells expressing the Wac protein fused with Histag: 1—Mass marker (Fermentas SM0661), 2, 3, 4, 5-unrelated, 6-WacHistag 3 h after IPTG induction (the product is marked with an arrow), Panel C—image of an electrophoretic gel—protein profile following the lysis of cells expressing the Wac protein fused with GST:1—Mass marker (Fermentas SM0661), 2, 3, 4—unrelated, 5-WacGST 3 h following IPTG induction (the product is marked with an arrow), Panel D—image of an electrophoretic gel—protein profile following the lysis of cells expressing the protein gp23* fused with GST:1—Mass marker (Fermentas SM0661), 2, 3-unrelated, 4-23*GST 3 h following IPTG induction (the product is marked with an arrow).

FIG. 5 shows the results obtained from a T4 bacteriophage preparation using competitive phage-display using a strain of *E. coli* expressing the recombinant protein gpWac and purification on a glutathione resin (dializa wstepna, fraction 2).

In FIG. 6 shows the results obtained from a a T4 bacteriophage preparation produced using competitive phage-display using a strain of *E. coli* expressing the recombinant protein gpWac and purification on a glutathione resin (no dialysis, fraction 1).

In FIG. 7 shows the results obtained from a T4 bacteriophage preparation using competitive phage-display using strain *E. coli* expressing the recombinant protein gp23* and purification on a glutathione resin (initial dialysis, fraction 1).

EXAMPLE 1

The procedure is based on the preparation and use of a parental bacteriophage strain without genetic alterations. The T4 bacteriophage host used was an expression strain of *Escherichia coli* trasnformed with expression plasmids containing a correct 23* gene or a correct wac gene fused with a sequence encoding a selected peptide motif for expression on the capsid. Such a bacteriophage culture is capable of competitively including proteins into the recombinant expression plasmid also expressed in the bacterium: gp23* fused with binding motif or gpWac fused with a binding motif. This results in stable capsid structures containing the recombinant protein, and thus containing and displaying a motif with a strong affinity for binding resins on their surface.

Two alternative methods of releasing bacteriophages from the resin may be used: (i) competitive elution, meaning displacement using compounds capable of interacting with the binding motif on the capsid and/or the binding resin (glutathione, imidazole), or (ii) proteolytic release using a protease that recognizes rare motifs. The second strategy requires that during the design of the expression plasmid construct for expressing the recombinant protein in the cell a sequence be introduced that is recognized by an appropriate protease. In the case of proteolytic binding, the bacteriophage capsid lacks a binding motif.

A detailed example embodiment of the method according to the present invention is given below.

Bacterial host cells have been obtained using an expression *Escherichia coli* strain, which were transformed with expression plasmids containing a correct 23* or wac gene fused with a sequence encoding a selected binding motif. In the example embodiment we used the plasmid pDEST15 (Invitrogen), which contained an expression cassette that made it possible to obtain a protein containing gp23* or gpWac fused with GST (FIG. 2) or an expression cassette encoding a protein containing gp23* or gpWac fused with Histag (FIG. 3).

Figure 4:
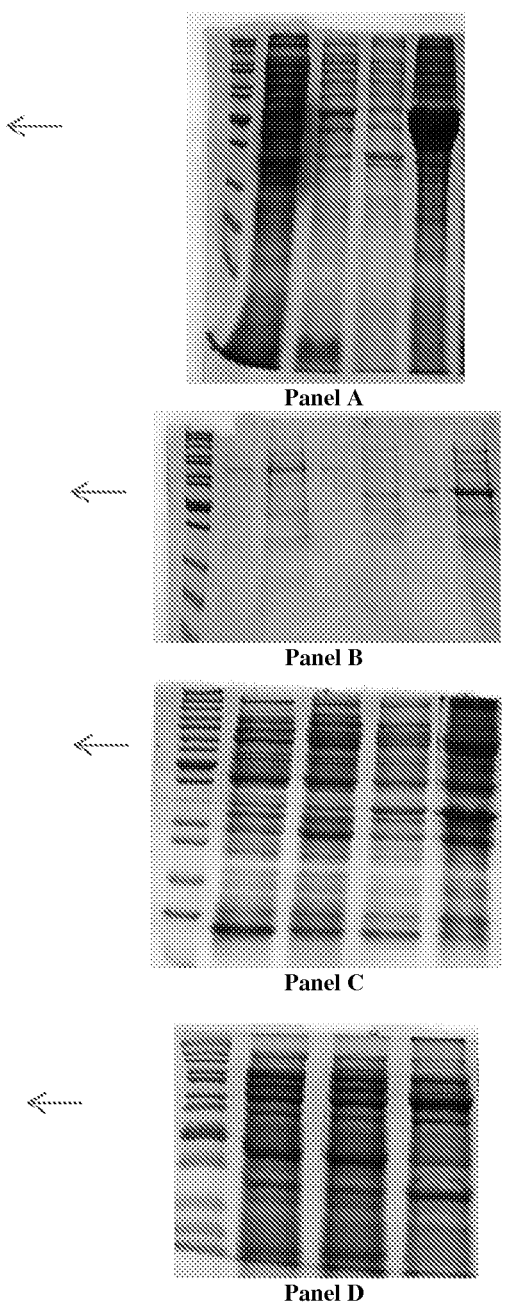

Te effectiveness of the transformation of *E. coli* Rosetta cells was examined observing the expression of gp23* or gpWac proteins fused with the tags GST and Histag (FIG. 4).

The recombinant bacterial host cells were cultured at a temperature of 37 C do $OD_{600}$ 0.7 on LB medium (LB-Broth, high salt) consisting of: enzymatic casein hydrolysate 10 g/l, yeast extract 5 g/l, sodium chloride 10 g/l, pH 7.5. Next, the cells were transferred into fresh LB (at a ratio of 1:100 in terms of LB) optionally: the culture was maintained to an $OD_{600}$=0.1, and supplemented with IPTG to 0.0025 M and 1:100 of the phage lysate HAP1 (~3×10$^9$ pfu/ml). The induction of expression and inoculation thus were simultaneous. The infected cells were cultured at 37 C at 160 RPM for 8-12 hours.

In the example embodiment described herein, the recombinant *Escherichia coli* were inoculated with wild T4 bacteriophages at the ame time inducing the expression of the Hoc proteins, and at the same time phage lysis and induction of the expression of the recombinant proteins gp23* or gpWac was performed.

The phage lysate was fietered, optionally dialysed into a phosphate buffer identical to that for eluting the columns on a 300 kDa pore membrane, whereafter they were incubated with an appropriate agarose resin: Glutathione sepharose or agaroses with metal ions that form complexes with imidazole histidine residues (i.e. agar NiNTA). The lysates were incubated with an appropriate resin overnight at a temperature of 4° C. with gentle rocking. After the unbound fraction was removed, a typical affinity chromatography purification procedure was used. The resin was rinsed in the buffer: 50 mM Na2HP04, 300 mM NaCl, pH 7.5 (GST resin) or 50 mM Na2HP04, 300 mM NaCl, 50-100 m M imidazole, pH 7.5 (nickel resin). Next, the bacteriophages were eluted or were released from the resin proteolytically.

In the case of GST, two elution methods are possible:
competitive elution with 40 mM reduced glutathione (fractions 1 or 2);
elution buffer: 40 mM reduced glutathione, 50 mM Tris, pH 8.0. Prior to collecting each fraction, the resin was incubated with the buffer for 20 minutes;
proteolytic release using the AcTEV protease;
the use of proteolytic release requires the preceding theoretical analysis of the sequence or and an empirical test for the sensitivity of a bacteriophage to the protease activity (controlled titre reduction); here we used a theoretical analysis based on the sequence analysis of the external T4 capsid proteins
protease buffer: 50 mM Tris, 0.5 mM EDTA, 1 mM OH, pH 8.0. The enzyme was supplied in athe amount of 5 µl per 1 ml złoża (activity—10 U/µl). Proteolysis was performed for 1 day at 4° C.

In the case of the NiNTA resin, the phage was displaced with imidazole in a 100-500 mM gradient (1 or 2 fractions)-elution buffer: 100-500 mM imidazole (depending on the fraction), 50 mM Na2HP04, 300 mM NaCl, pH 7.5 The rinsing and elution was performed at room temperature.

Methods of Analyzing the Results

The specificity of bacteriophages modified in terms of the affinity resin was examined based on a comparison of the elution profile of T4 phages modified with a tag specific for a given resin and a tag not compatible with the resin. The elution profile was determined by evaluating the phage titre in the individual fractions. As a control, we determined the phage titre in the last fraction of the elution buffer. The experiment was viewed as successful on the assumption that the titre in said fraction was no greater than 1% of the bound phages, as detected in the previously eluted fractions. The effectiveness of the purification was determined by determining the level of endotoxins eluted (or released) in the fractions.

Results

The results obtained are shown in the Figures and Table contained in the present description The curves shown in the show a comparison of selected elate fractions. In the case of comparative experiments, which were to confirm the specificity of a phage to a resin, the initial titres of the control and potentially specific preparations were identical. Identical volumes of lysates were incubated with the same volume of resin, rinsed and eluted in the same conditions.

Figure 5:
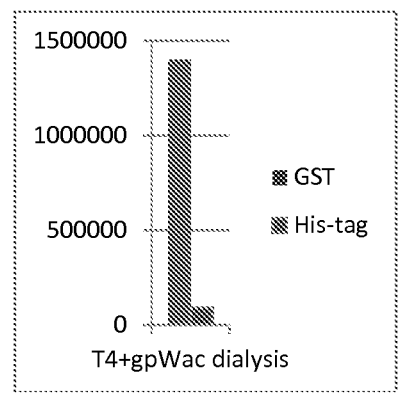

FIG. 5 represents a comparison of the T4 bacteriophage preparations using competitive phage-display using an *E. coli* strain expressing the recombinant protein gpWac and purification on a glutathione resin (initial dialysis, fraction 2). The affinity of the specifically tagged (GST) preparation for the resin exceeds the affinity of the preparation tagged with the non-specific tag (His-tag) over 15-fold, which is evidence of the specific binding of a phage modified with the GST tag.

Figure 6:
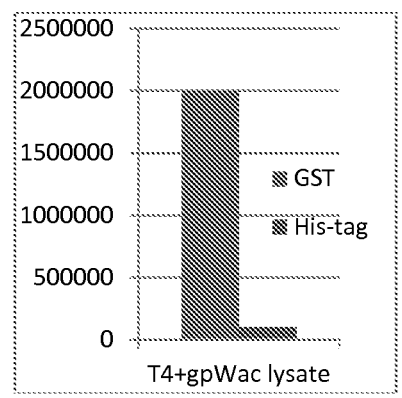

FIG. 6 represents a comparison of the T4 bacteriophage preparations using competitive phage-display using an *E. coli* strain expressing the recombinant protein gpWac and purification on a glutathione resin (no dialysis, fraction 1) The affinity of the specifically tagged (GST) preparation for the resin exceeds the affinity of the preparation tagged with the non-specific tag (His-tag) over 20-fold, which is evidence of the specific binding of a phage modified with the GST tag.

Figure 7:
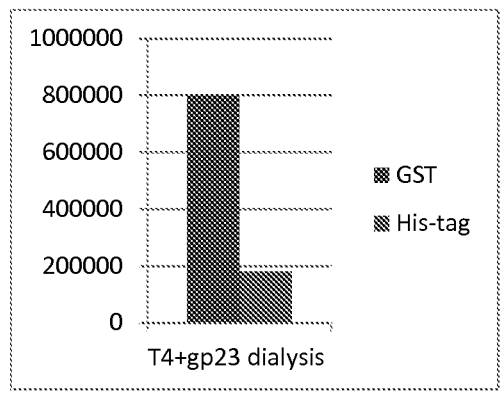

FIG. 7 represents a comparison of the T4 bacteriophage preparations using competitive phage-display using an *E. coli* strain expressing the recombinant protein gp23* and purification on a glutathione resin (initial dialysis, fraction 1). The affinity of the specifically tagged (GST) preparation for the resin exceeds the affinity of the preparation tagged with the non-specific tag (His-tag) over 4.5-fold, which is evidence of the specific binding of a phage modified with the GST tag.

Figure 8:
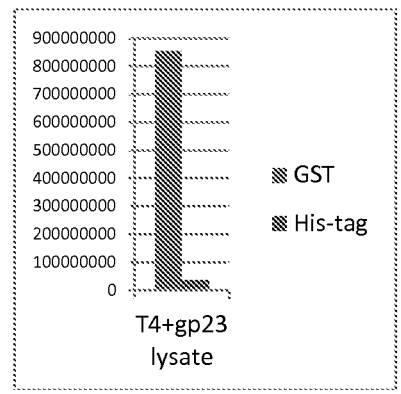
FIG. 8 shows the results obtained from a T4 bacteriophage preparation using competitive phage-display using strain *E. coli* expressing the recombinant protein gp23* and purification on a glutathione resin (no dialysis, fraction 1).

FIG. 8 represents a comparison of the T4 bacteriophage preparations using competitive phage-display using an *E. coli* strain expressing the recombinant protein gp23* and purification on a glutathione resin (no dialysis, fraction 1) The affinity of the specifically tagged (GST) preparation for the resin exceeds the affinity of the preparation tagged with the non-specific tag (His-tag) over 24-fold, which is evidence of the specific binding of a phage modified with the GST tag.

Figure 9:
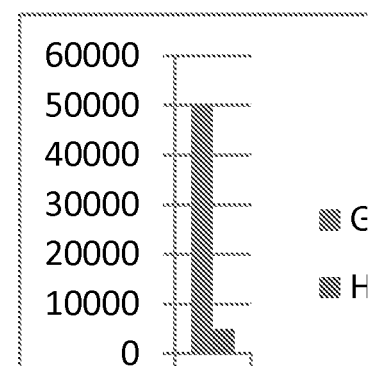
FIG. 9 shows the results obtained from a T4 bacteriophage preparation using proteolytic digestion (1 day), using competitive phage-display using an *E. coli* strain expressing the recombinant protein gp23* and purification on a glutathione resin (dializa).

FIG. 9 represents a comparison of the T4 bacteriophage preparations, using proteolytic digestion with AcTev and competitive phage-display using an *E. coli* strain expressing the recombinant protein gp23* and purification on a glutathione resin (dialysis). The affinity of the specifically tagged (GST) preparation for the resin exceeds the affinity of the preparation tagged with the non-specific tag (His-tag) over 10-fold, which is evidence of the specific binding of a phage modified with the GST tag.

Figure 10:
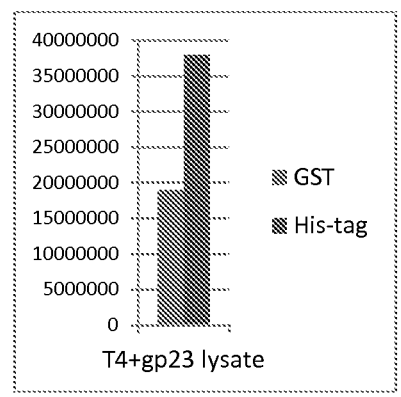
FIG. 10 shows the results obtained from a T4 bacteriophage preparation using competitive phage-display using an *E. coli* strain expressing the recombinant protein gp23* and purification nickel-agarose resin NiNTA (no dialysis, fraction 1)

FIG. 10 represents a comparison of the T4 bacteriophage preparations using competitive phage-display using an *E. coli* strain expressing the recombinant protein gp23* and purification on a glutathione resin (no dialysis, fraction 1). The affinity of the specifically tagged (His-tag) preparation for the resin exceeds the affinity of the preparation tagged with the non-specific tag (GST) over 2-fold, which is evidence of the specific binding of a phage modified with the His-tag tag.

TABLE 1

The table represents the obtained endotoxin values for the purified phage preparations and their corresponding titres.

| Phage preparation | Endotoxin level (EU/ml) |
| --- | --- |
| Elution: T4 modified with GST fused with gp23*, Lizat | 1000 |
| Elution: T4 modified with GST fused with gp23*, dialysed | 24 |
| Elution: T4 modified with GST fused with gpWac, lysate | 88 |
| Elution: T4 modified with GST fused with gpWac, dialysed | 51 |
| Elution: T4 modified with Histag fused with gp23 *, lysate | 1000 |
| Proteolysis: T4 modified with GST fused with gp23*, dialysis | 38 |

CONCLUSIONS

The proposed method facilitates the single-stage and at the same time effective purification of phage preparations, while maintaining the antibacterial activity of bacteriophages, both in the case of a strategy based on the displacement of bacteriophages from a resin as well as proteolytic release. It does not require separate steps for the removal of proteinaceous and non-proteinaceous (here: LPS) contaminants. The modification of the phage capsid with appropriate binding motifs may also facilitate the purification of other bacteriophage strains using affinity chromatography. The proposed method facilitates the presentation of selected peptides or proteins on a phage not genetically modified for the purposes of phage-display, i.e. wild-type strains occurring naturally, or others (i.e. lab strains of various purposes).

The invention claimed is:

1. A method of producing therapeutic bacteriophages for treatment of bacterial infections in a subject in need thereof comprising:
   a) preparing a bacterial host cell culture by culturing a bacterial host cell on a medium,
   b) inoculating the bacterial host cell culture with a parent bacteriophage source to produce a bacteriophage lysate comprising a progeny bacteriophage containing a fusion protein encoded by SEQ ID NO: 2 or SEQ ID NO: 3, and
   c) purifying the progeny bacteriophage from the lysate using affinity chromatography,
   wherein the bacterial host cell is transformed with a plasmid containing said SEQ ID NO: 2 or SEQ ID NO: 3, a structural phage protein and a foreign peptide having an affinity for the chromatography resin of stage c);
   wherein the parent bacteriophage source is a wild-type bacteriophage;
   wherein the foreign peptide is HisTag or GST; and
   wherein the progeny bacteriophage resulted from stage c) contains a wild-type phage genome.

2. The method according to claim 1, wherein during stage a) the bacterial host cell culture is conducted on a culture medium with a pH of about 7.2 and containing a meat extract, enzymatic casein hydrolysate, yeast hydrolysate, peptone and NaCl.

3. The method according to claim 1, wherein stage a) the bacterial host cell used is a bacterial cell sensitive to the lytic activity of the amplified bacteriophage.

4. The method according to claim 1, further comprising a filtration step for the lysate between stage b) and stage c), the filtration step being performed by passing the lysate through a 0.22 μm sterilizing filter.

5. The method of claim 1, wherein the structural phage protein is the polypeptide encoded by SEQ ID NO: 1.

6. The method of claim 1, further comprising inducing expression of the fusion protein in step (a).

7. The method of claim 6, wherein said inducing expression of the fusion protein takes place simultaneously with said inoculating the bacterial host cell culture.

* * * * *